United States Patent
Knoblich

(10) Patent No.: US 8,219,189 B2
(45) Date of Patent: Jul. 10, 2012

(54) METHOD AND APPARATUS FOR IMPROVING RENAL FUNCTION

(76) Inventor: Penny Knoblich, Mankato, MN (US)

(\*) Notice: Subject to any disclaimer, the term of this patent is extended or adjusted under 35 U.S.C. 154(b) by 560 days.

(21) Appl. No.: 12/460,286

(22) Filed: Jul. 16, 2009

(65) Prior Publication Data

US 2009/0326613 A1  Dec. 31, 2009

Related U.S. Application Data

(63) Continuation-in-part of application No. 11/001,423, filed on Dec. 1, 2004, now abandoned.

(51) Int. Cl.
*A61N 1/18* (2006.01)

(52) U.S. Cl. .................................................. 607/2

(58) Field of Classification Search .............. 607/1–2, 607/44, 48, 117
See application file for complete search history.

(56) References Cited

U.S. PATENT DOCUMENTS

2003/0216792 A1\* 11/2003 Levin et al. ..................... 607/48
2004/0220621 A1\* 11/2004 Zhou et al. ....................... 607/2

\* cited by examiner

*Primary Examiner* — Carl H Layno
*Assistant Examiner* — Jessica Sarcione
(74) *Attorney, Agent, or Firm* — Beck & Tysver, PLLC

(57) ABSTRACT

A method for improving renal function includes placing an electrode on a dorsal spinal cord within a central nervous system and applying an electrical current to the electrode. The electrode is positioned, and the electrical current is configured, to stimulate an afferent neuron without stimulating an efferent neuron, thereby causing an increase in renal excretion of sodium and water while having an insubstantial affect on a sympathetic nervous system.

20 Claims, 5 Drawing Sheets

METHOD AND APPARATUS FOR IMPROVING RENAL FUNCTION

CROSS-REFERENCE TO RELATED APPLICATION(S)

This application is a continuation-in-part of U.S. patent application Ser. No. 11/001,423 filed Dec. 1, 2004 and entitled "Method and Apparatus for Improving Renal Function" now abandoned.

BACKGROUND

The present invention relates generally to stimulation of body tissue for a therapeutic effect on body organs, and more particularly to electrical stimulation of neurons for improving renal function.

The kidneys are essential organs located at the back of the abdomen on each side of the spinal column at about the level of the lower ribs. The kidneys receive about twenty percent of total cardiac output and function to remove waste products from the blood and regulate blood electrolytes, acid-base balance, total body water, and blood volume.

The basic functional unit of the kidney is the nephron. Each nephron includes a glomerulus, a capillary through which blood flows and from which fluid is filtered. Filtered fluid enters the tubules, which process the fluid. At the end of the tubules, the filtered fluid ultimately becomes urine. The standard measure of renal function is the glomerular filtration rate, or the total rate that fluid is filtered from all the glomeruli combined. The normally functioning kidney controls the blood electrolytes, acid-base balance, total body water, and blood volume by adjusting the reabsorption (back into the body) or secretion (from the body into the filtered fluid) of electrolytes, acids and bases, and water. If excess water is present in the body, it is excreted in the urine. If excessive solutes are present in the body, they are excreted preferentially. In spite of large intakes of either water or salt, the normal kidney can accommodate and precisely regulate the volume and composition of the blood.

Although the primary measure of kidney function relates to excretion it is important to note that the kidneys also function to produce hormones. The kidneys are in part responsible for the conversion of Vitamin D to its active metabolite, a hormone that functions to increase the absorption of calcium from the intestines. The kidneys also synthesize erythropoietin, a stimulating hormone for red blood cell production, and renin, a hormone involved in the regulation of sodium reabsorption and the maintenance of blood pressure.

Proper elimination of sodium from the body is one of the critical functions of the kidney. Failure of the kidneys to adequately eliminate sodium increases total body sodium and water, and blood volume. The increase in blood volume raises pressure in the vascular system, producing hypertension, or high blood pressure.

Progressive renal failure, occurring as a result of a variety of disorders, can give rise to a number of symptoms which decrease both the length and quality of life. Vascular damage to the glomeruli, infiltration of the renal tissues with inflammatory cells, and damage and scarring of the tubules, all contribute to the degeneration of renal function. Pathological processes primarily affecting the vasculature, such as diabetes mellitus, hypertension, overuse of over-the-counter anti-inflammatory medications, and side-effects of some pharmaceutical agents, preferentially damage the glomeruli. Chronic inflammation, repeated infection, or certain poisons may damage the tubular system. Renal failure is typically characterized by a progressive inability to maintain normal electrolyte composition, blood pH, and body water volume. Sodium chloride, or salt, becomes progressively more difficult to eliminate from the body. Concomitant interactions increase blood volume and pressure, cause acidosis, and produce edema in body tissues.

SUMMARY

An apparatus embodiment of the present disclosure is a device for improving renal function including a first electrode, a second electrode, and a pulse generator. The first electrode is positioned in a central nervous system, on a dorsal spinal column at a vertebral level associated with a kidney sensory nerve-central nervous system pathway. The second electrode is positioned in a paravertebral muscle proximate the first electrode. The pulse generator is in electrical communication with the first electrode and the second electrode for delivering an electrical current therebetween. The pulse generator is programmed to determine a motor threshold of the paravertebral muscle, and deliver a therapeutic electrical current between the first electrode and the second electrode. The therapeutic electrical current having an amplitude, duration, and waveform derived from, and expressed as a fraction of, the motor threshold of the paravertebral muscle. The therapeutic electrical current stimulating at least one afferent sensory neuron and causing a rapid increase in renal excretion of sodium and water.

Another embodiment of the present disclosure is a method for improving renal function. The method includes placing a first electrode on a dorsal spinal column within a central nervous system at a vertebral level associated with a kidney sensory nerve, and placing a second electrode in a paravertebral muscle proximate the first electrode. The method further includes measuring a motor threshold of the paravertebral muscle, and applying an electrical current to at least one afferent sensory neuron. The electrical current has parameters (e.g. current, voltage, and/or waveform) derived from the motor threshold. Application of the electrical current causes a rapid increase in renal excretion of sodium and water as compared to a baseline taken before application of the electrical current.

In yet another embodiment, a method for improving renal function includes placing an electrode on a dorsal spinal cord within a central nervous system and applying an electrical current to the electrode. The electrode is positioned, and the electrical current is configured, to stimulate an afferent neuron without stimulating an efferent neuron, thereby causing an increase in renal excretion of sodium and water while having an insubstantial affect on a sympathetic nervous system.

DETAILED DESCRIPTION

Historically, the treatment of kidney failure addressed secondary symptoms rather than directly impacting the function of the kidneys themselves. For example, diuretics are commonly used to reduce blood volume and pain medication is commonly used to manage pain. End stage kidney disease is typically also treated by hemodialysis, in which the blood is "cleaned" by exchange with a dialysis fluid across a selectively permeable membrane. In contrast to pharmacological treatments of renal dysfunction and hemodialysis as a treatment for end stage renal disease, the present disclosure relates to the use of electrical stimulation of specific neuronal pathways to alter and improve renal function. The method and apparatus described herein has been implemented in an animal model. Human treatment modalities and implantable electrical stimulator embodiments are anticipated.

Figure 1:
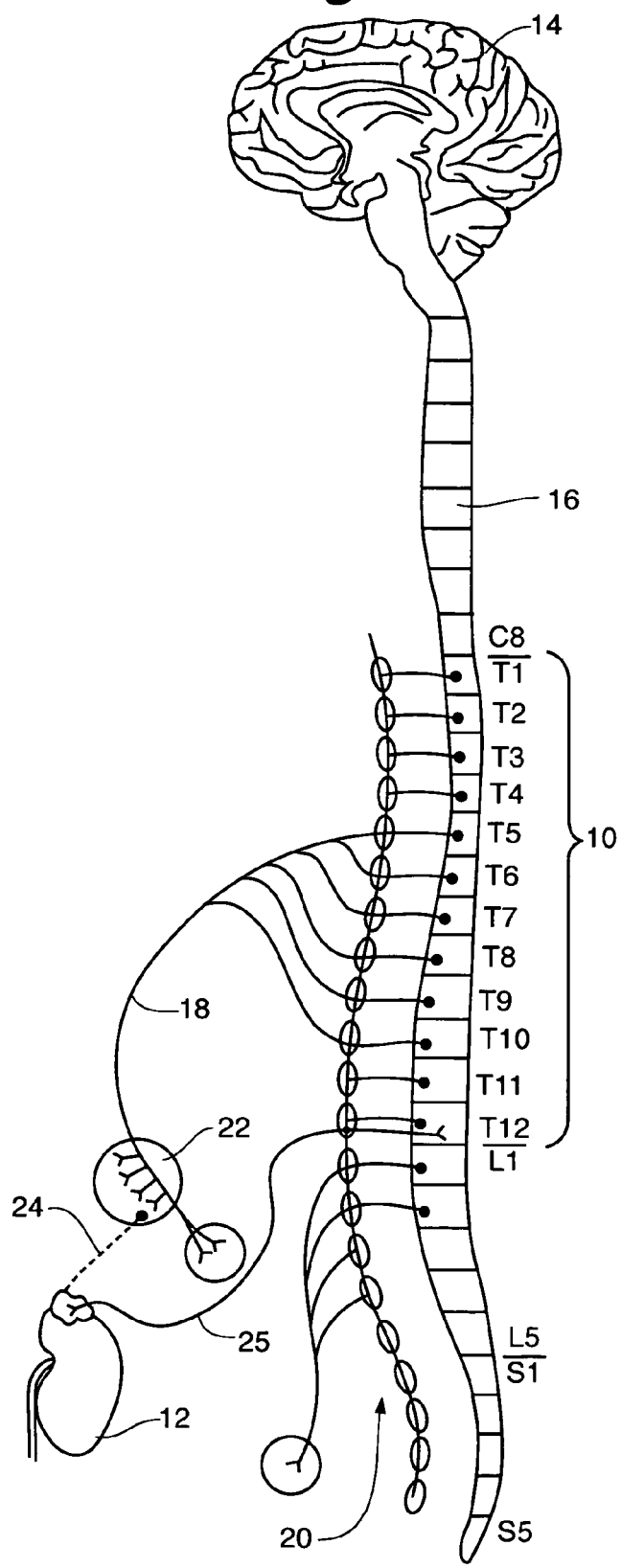
FIG. 1 is a side view of a nervous system schematically showing neural innervation of a kidney.

FIG. 1 is a side view of sympathetic nervous system (SNS) 10 schematically showing neural innervation of kidney 12. Depicted in FIG. 1 are: SNS 10, kidney 12, brain 14, spinal column 16, preganglionic neuron 18, sympathetic trunk 20, autonomic ganglion 22, postganglionic neuron 24, and sensory neuron 25. SNS 10 receives information from brain 14 and sends information from spinal column 16 out to kidney 12 via preganglionic neuron, sympathetic trunk 20, autonomic ganglion 22, and postganglionic neuron 24. In contrast, sensory neuron 25 transmits information from kidney 12 to spinal column 16 and brain 14.

The organs of the body, including kidney 12, are innervated by an elaborate nervous system that can be subdivided both anatomically and physiologically. Anatomically speaking, the nervous system is divisible into a central nervous system (CNS) and a peripheral nervous system (PNS). The CNS consists of brain 14 and spinal column 16, while the PNS consists of all non-CNS nervous structures, including outgoing (efferent-sympathetic) nerves such as elongated axon of preganglionic neuron 18 (note cell body of preganglionic neuron 18 is within CNS), autonomic ganglion 22, and postganglionic neuron 24, and incoming (afferent-sensory) nerves, such as sensory neuron 25. Physiologically speaking, the two parts of the peripheral nervous system are very different, with an afferent division bringing sensory information into the CNS, and an efferent division bringing motor information out of the CNS. The efferent division is further divisible into a somatic nervous system that coordinates voluntary motor movements and an autonomic nervous system that effectuates involuntary physiological processes. The autonomic nervous system is further divisible into a sympathetic nervous system (SNS) 10 configured to mobilize the body in fight or flight situations which is schematically depicted in FIG. 1, and a parasympathetic nervous system (PNS) that promotes everyday "housekeeping" functions during periods of rest.

Previous research has demonstrated that SNS 10 has a multitude of effects on kidney 12. SNS 10 has been shown to reduce total renal blood flow, increase renin release (resulting ultimately in an increase in the reabsorption of sodium), and change the distribution of blood flow between the outer renal cortex and inner medulla (altering sodium reabsorption). The SNS is a two neuron system, which means that a "first" or preganglionic nerve 18 originates in the central nervous system and travels only part way to the innervated tissue, and a "second" or postganglionic nerve 24 traverses the remaining distance. The junctions or synapses between first and second nerves take place in a multitude of ganglia, dispersed along the spinal column (paravertebral ganglia or sympathetic trunk 20). SNS innervation of the kidney 12 arises from the ipsilateral paravertebral sympathetic trunk 20 in an area spanning between thoracic vertebra 4 and lumbar vertebrae 1, with the peak output coming from the $10^{th}$ thoracic vertebra. SNS 10 information originates in the CNS and leaves spinal column 16 at by way of preganglionic neuron 18. The cell body of preganglionic neuron 18 lies within the lateral horn of the gray matter of the spinal cord 16, but the elongated axon of preganglionic neuron 18 extends via the ventral horn through sympathetic trunk 20 and synapses onto postganglionic neuron 24 at autonomic (paravertebral) ganglion 22. Postganglionic neuron 24 extends from its synaptic junction with preganglionic neuron 18 and joins with sensory fibers from kidney 12 to form a spinal nerve, which at this point contains both afferent and efferent fibers. The sympathetic fibers continue in the spinal nerve toward kidney 12 and ultimately synapse onto kidney 12. Kidney 12 function depends not only upon electro-chemical signals delivered through these efferent neurological pathways of SNS 10, but also on cytokines and other signal molecules produced locally within kidney 12, and/or circulating in the blood. The complexities of kidney 12 neuronal innervation and physiology make it difficult to fully predict or understand the impact of either pharmaceutical or electrical therapy on renal function.

Figure 2:
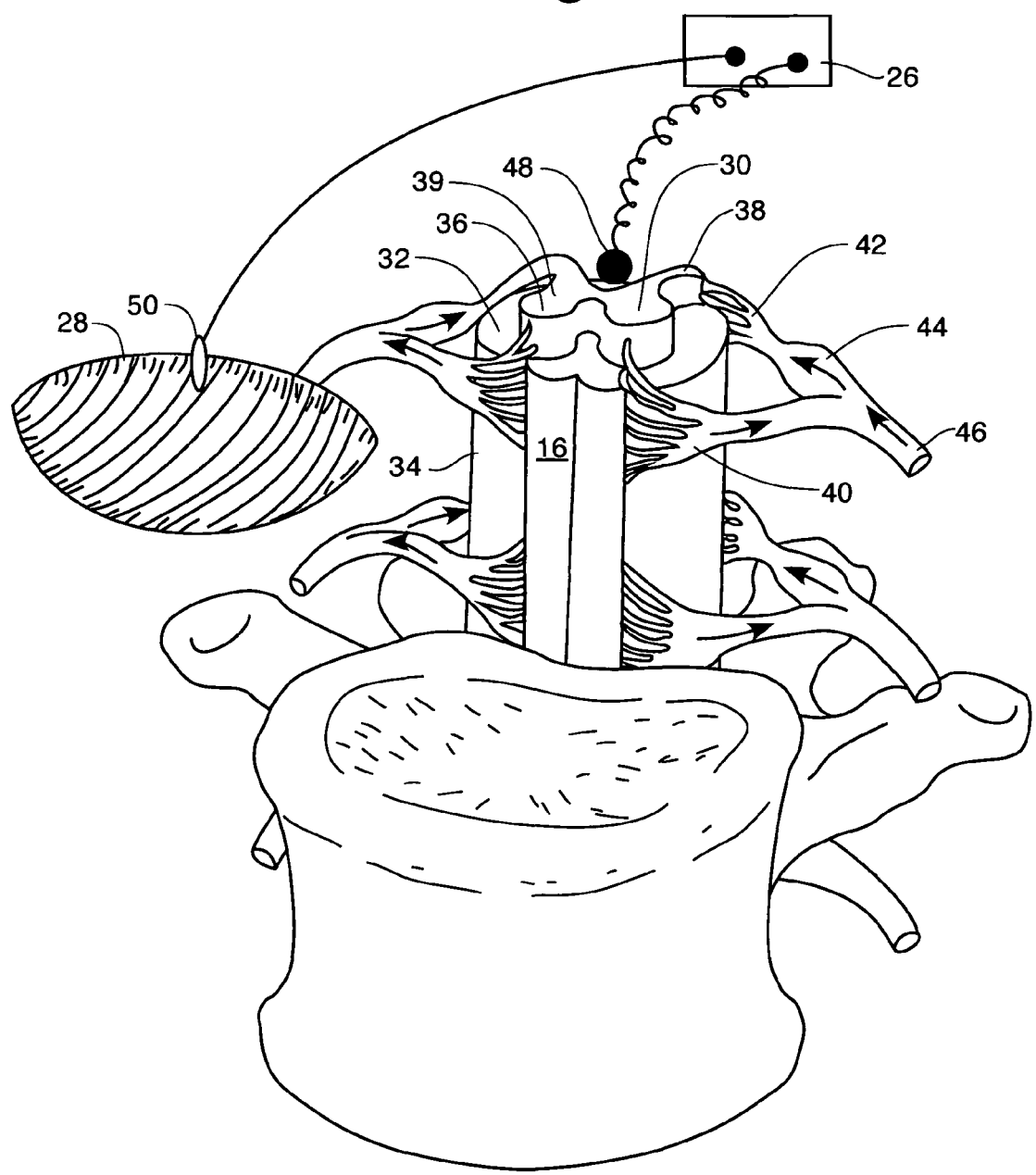
FIG. 2 is a ventral cross-section of a spinal column showing anatomical placement for electrodes in accordance with an embodiment of the present disclosure.

FIG. 2 is a ventral cross section of spinal cord or column 16 schematically showing placement for electrodes 48, 50 in accordance with the present disclosure. Depicted in FIG. 2 are spinal cord 16, programmable stimulator 26, and paravertebral muscle 28. Spinal cord 16 is a main component of the CNS and includes gray matter 30 (containing nerve cell bodies), white matter 32 (consisting of nerve axons), dura mater 34, ventral horn 36 (containing motor nerve cell bodies), dorsal horn 38 (containing the synapses between the sensory nerves and central nerves), and lateral horn 39 (containing sympathetic preganglionic nerve cell bodies). Ventral root 40 (efferent sympathetic and motor axons), dorsal root 42 (sensory nerve axons) dorsal root ganglion 44 (sensory nerve cell bodies), and spinal nerve 46 (both afferent and efferent axons) are all components of the PNS extending outwardly from spinal cord 16 to connect with tissues. Programmable stimulator 26 includes two electrodes: ball electrode 48 and needle electrode 50. Programmable stimulator 26 operates to stimulate neurons on a dorsal side of spinal cord 16 thereby improving renal function.

Spinal cord 16 is generally protected by bony vertebrae, which collectively comprise a spine or backbone. Paravertebral muscle 28 lies dorsal and lateral to the vertebrae and functions to facilitate flexion and extension of the spine. An inner layer of spinal cord 16, known as gray matter 30, contains interneurons (small neurons), cell bodies and dendrites of outgoing efferent neurons (ventral and lateral horns), entering axons of incoming afferent neurons (dorsal horns), and glial cells. Surrounding gray matter 30 is white matter 32 consisting largely of myelinated axons running longitudinally through spinal cord 16, carrying information upward toward the brain (afferent or sensory), or downward from brain to spinal cord (efferent or motor) in discrete anatomical locations known as ascending (upward) or descending (downward) tracts. Surrounding white matter 32 is dura mater 34, which is the protective outer covering of spinal cord 16. A most ventral portion of gray matter 30 is called ventral horn 36, a most dorsal portion of gray matter 30 is called dorsal horn 38, and a most lateral portion of gray matter 30 is called lateral horn 39. Efferent motor neurons E have cell bodies located in or near ventral horn 36 and axons of these efferent neurons generally leave spinal column 16 at ventral root 40. Efferent sympathetic neurons have their cell bodies located in the lateral horn 39, and their axons also exit from ventral root 40. In contrast, the cell bodies of afferent neurons A are generally located in dorsal root ganglion 44 (outside the spinal cord) and axons of these afferent neurons A enter spinal column 16 through dorsal root 42, and synapse on central nerves in dorsal horn 38. Central nerve axons then carry the sensory information to the brain, traveling in the white matter in ascending tracts. Dorsal root 42 and ventral root 40 join medially to form spinal nerve 46 and exit the bony vertebrae together. Of particular relevance to dorsal spinal electrical stimulation are the dorsal spinal columns in white matter 32 that lie just beneath dura mater 34 on the dorsal surface of spinal cord 16, and carry sensory information to the brain.

In accordance with the present invention, programmable stimulator 26 can be implanted in, or located externally to, a body to improve renal function. Bony matter such as a spinal process can be surgically removed to provide access to spinal cord 16. Electrode ball (cathode) 48 is placed on dura matter 34 on a dorsal side of spinal cord 16 to stimulate afferent (sensory) neurons A and/or afferent central neurons traveling in white matter 34 dorsal ascending tracts (dorsal columns), and needle electrode (anode) 50 is inserted into nearby paravertebral muscle 28. Electrical leads electrically connect both electrodes 48, 50 to programmable stimulator 26. Programmable stimulator 26 can be hermetically sealed and implanted internally, or left external to the subject. In one embodiment, stimulator 26 includes a lithium battery powered electronics package, which can be remotely programmed to provide electrical stimulation to both electrode ball 48 and needle electrode 50 and carry out a method in accordance with the present disclosure. Once electrodes 48, 50 become permanent or chronic, it is advisable to re-determine motor thresholds and/or titrate the effective dose for the therapeutic method described below.

Experimental work carried out in a laboratory used stimulator 26 and two electrodes 48, 50 to deliver current between electrodes 48, 50. An alternative embodiment using three electrodes where motor threshold of paravertebral muscle 28 can be measured independently of ball electrode 48 is contemplated. In this alternative embodiment, the "can" functions as an indifferent or ground electrode. The indifferent can/electrode could be used for both determining a threshold of paravertebral muscle 28 and again for therapeutic neural stimulation. This alternative architecture is speculative since the proposed mechanism of action has not been verified. It is possible that the current electrical path between two electrodes 48, 50 is important to the excretory results observed in the laboratory.

Figure 3:
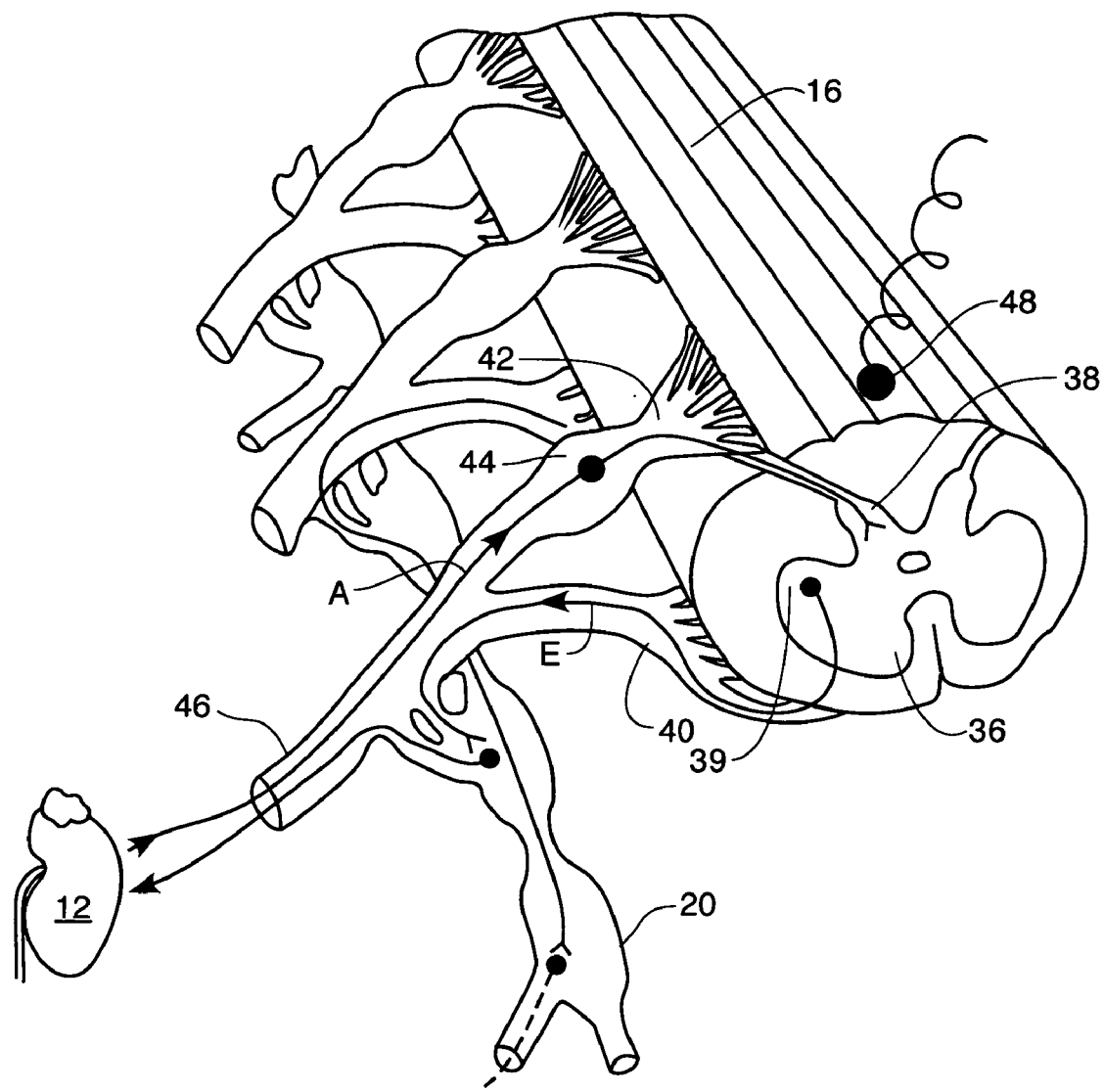
FIG. 3 is a dorsal perspective view of the spinal column further detailing the placement of an electrode with respect to specific neuronal pathways.

FIG. 3 is a dorsal perspective view of spinal column 16 and sympathetic trunk 20 further detailing the placement of electrode ball 48 with respect to specific neuronal pathways. Depicted in FIG. 3 are kidney 12, spinal cord 16, sympathetic ganglion 20, ventral horn 36, dorsal horn 38, lateral horn 39, ventral root 40, dorsal root 42, dorsal root ganglion 44, spinal nerve 46, electrode ball 48, afferent neurons A, and efferent neurons E. Electrode ball 48 is positioned to stimulate afferent (sensory) neurons A on a dorsal side of spinal column 16 within the CNS to increase excretion of water and sodium by kidney 12.

Running alongside and parallel to spinal column 16 is sympathetic ganglion 20, which are collections cell bodies and axons located in the PNS just outside of the CNS. Slightly lateral to sympathetic ganglion 20 is spinal nerve 46, which is also a part of the PNS. When followed laterally and distally, spinal nerve 46 branches into renal nerve full of both efferent neurons E carrying information from the CNS to kidney 12 (such as postgaglionic neuron 24 depicted in FIG. 1) and afferent neurons A carrying information from kidneys 12 into the CNS. When followed medially and proximally (or toward spinal column 16), spinal nerve 46 branches into separate efferent and afferent neuronal pathways carrying efferent neurons E and afferent neurons A, respectively. The efferent pathway connects spinal nerve 46 to ventral root 40 and the afferent pathway connects spinal nerve 46 to dorsal root 42 through dorsal root ganglion 44. For example, efferent neurons E have cell bodies located within spinal cord 16, in either ventral horn 36 or lateral horn 39, axons that extend outwardly through ventral root 40 follow the efferent neuronal pathway to spinal nerve 46 and ultimately innervate kidney 12 (see SNS described in FIG. 1). In contrast, incoming sensory information from kidney 12 travels up spinal nerve 46, through the afferent neuronal pathway, leaves the spinal nerve to form dorsal root 42, and reaches the sensory cell bodies in the dorsal root ganglia 44. The information then continues on the axons of the sensory nerves which project through dorsal root 42 to enter spinal cord 16, synapse in dorsal horn 44, and ultimately be processed by the CNS. Electrode ball 48 is positioned on the dura matter of the dorsal side of spinal column 16 to stimulate specific afferent sensory neurons A entering the CNS.

Electrode ball 48 is positioned on dorsal spinal column 16 so that it has no direct affect, either excitatory or inhibitory, on efferent (outgoing, motor) neurons E. To be clear, the presently disclosed method and apparatus do not stimulate spinal nerve 46, sympathetic ganglion 20, efferent neurons E in efferent pathway, ventral horn 40, or lateral horn 39. Electrode ball 48 provides stimulation only to dorsal spinal column 16, thereby affecting only the afferent (incoming, sensory) neurons A. Electrical stimulation of afferent neurons A located within dorsal spinal column 16 resulted in perplexing and counter-intuitive effects on renal excretion of sodium to be discussed below with respect to FIG. 5.

Figure 4:
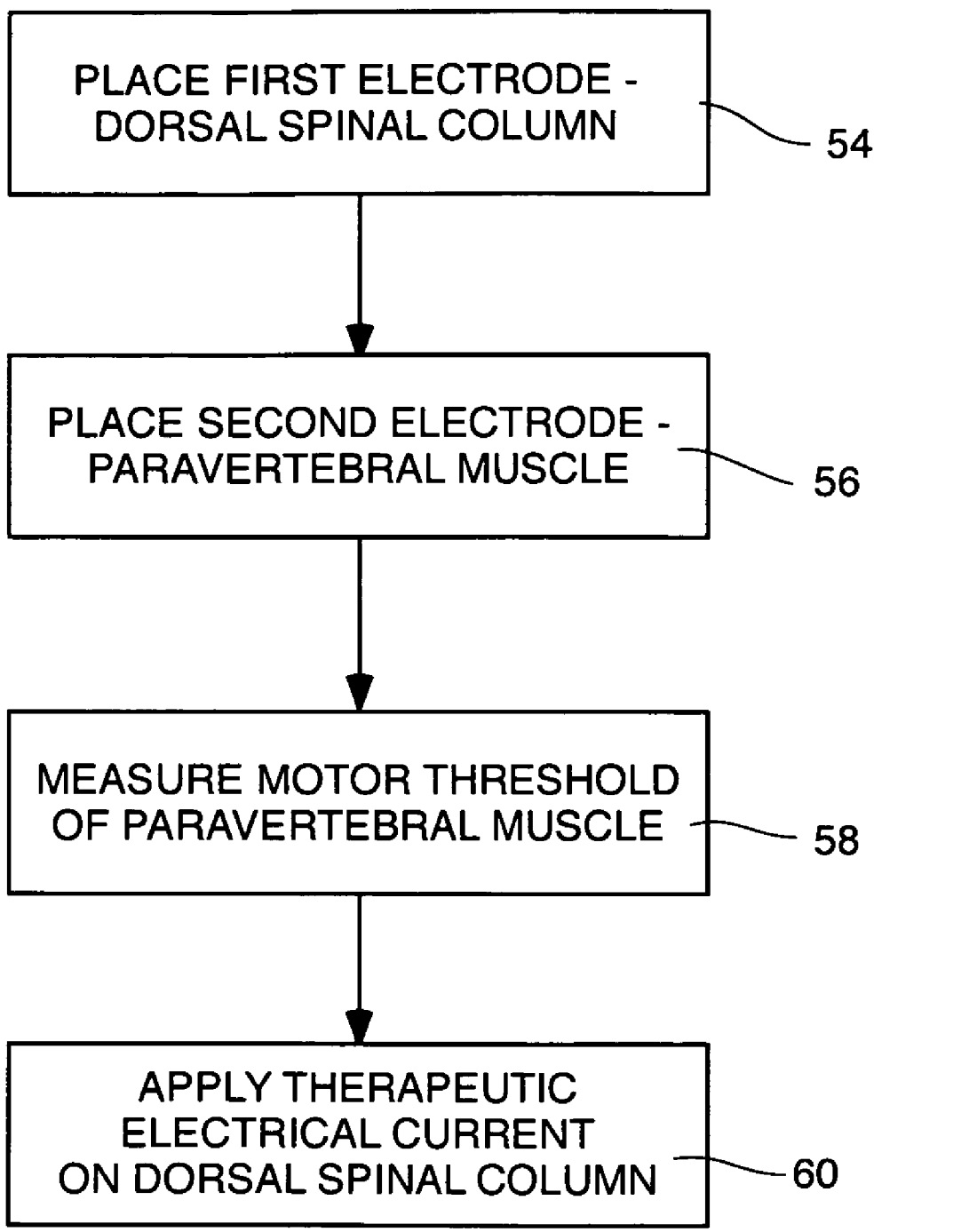
FIG. 4 is a flow chart representing a method for improving renal function in accordance with the present disclosure.

FIG. 4 is a flow chart representing method 52 for improving renal function in accordance with the present invention. Method 52 includes: placing a first electrode on a dorsal spinal column within the CNS at a vertebral level associated with a kidney sensory nerve (step 54) and placing a second electrode in a paravertebral muscle proximate the first electrode (step 56). The method further includes measuring a motor threshold of the paravertebral muscle (step 58) and applying a therapeutic electrical current to at least one afferent sensory neuron (step 60). The therapeutic electrical current (step 60) has parameters derived from the motor threshold (step 58). Application of electrical current to the afferent sensory neuron (step 60) causes a rapid increase in renal excretion of sodium and water as compared to a baseline taken before application of the therapeutic electrical current. Some experimentation with voltage and current levels is expected to compensate for differences in lead configuration and electrode impedance, as well as individual subjects.

During diagnosis and in preparation for therapy, method 52 is used to determine therapeutic electrical stimulation parameters for a particular subject. A first electrode, such as ball electrode 48, is placed on a dorsal spinal column 16 (step 54). The anatomical placement of first location is detailed above with reference to FIGS. 2 and 3. A second electrode, such as needle electrode 50, is placed on or in paravertebral muscle 28 proximate the first electrode (step 56). After implantation of the electrodes, the therapeutic stimulus strength (voltage and/or current) is determined by first finding the minimum voltage and/or current associated with activation and contraction of paravertebral muscle 28, commonly known as "motor threshold" (step 58). The motor threshold can be determined by slowly increasing the voltage and/or current delivered from programmable stimulator 26 to ball electrode 48 and needle electrode 50 until contraction of paravertebral muscle 28 is evident. In animal models, current and voltage in the range of about 1.2 volts to about 2.0 were proven effective. The electrical stimulus applied had a monophasic square sine wave pattern with a frequency of about 50 Hz, and a duration of about 0.2 milliseconds. Once the motor threshold for paravertebral muscle 28 is established, parameters for therapeutic electrical stimulation are deduced. Therapeutic stimulus strength is believed to be between about 30 to about 90 percent of motor threshold. When programmable stimulator 26 delivered therapeutic electrical stimulation to ball electrode 48 and needle electrode 50 having a stimulus strength equal to about 67 percent of motor threshold for paravertebral muscle, a dramatic increase in sodium and water excretion was noted (step 60). This therapeutic benefit of increased renal excretion (measured in micromoles per kilogram per minute) extended well beyond the cessation of the stimulus, which is discussed further with regards to FIG. 5.

Figure 5:
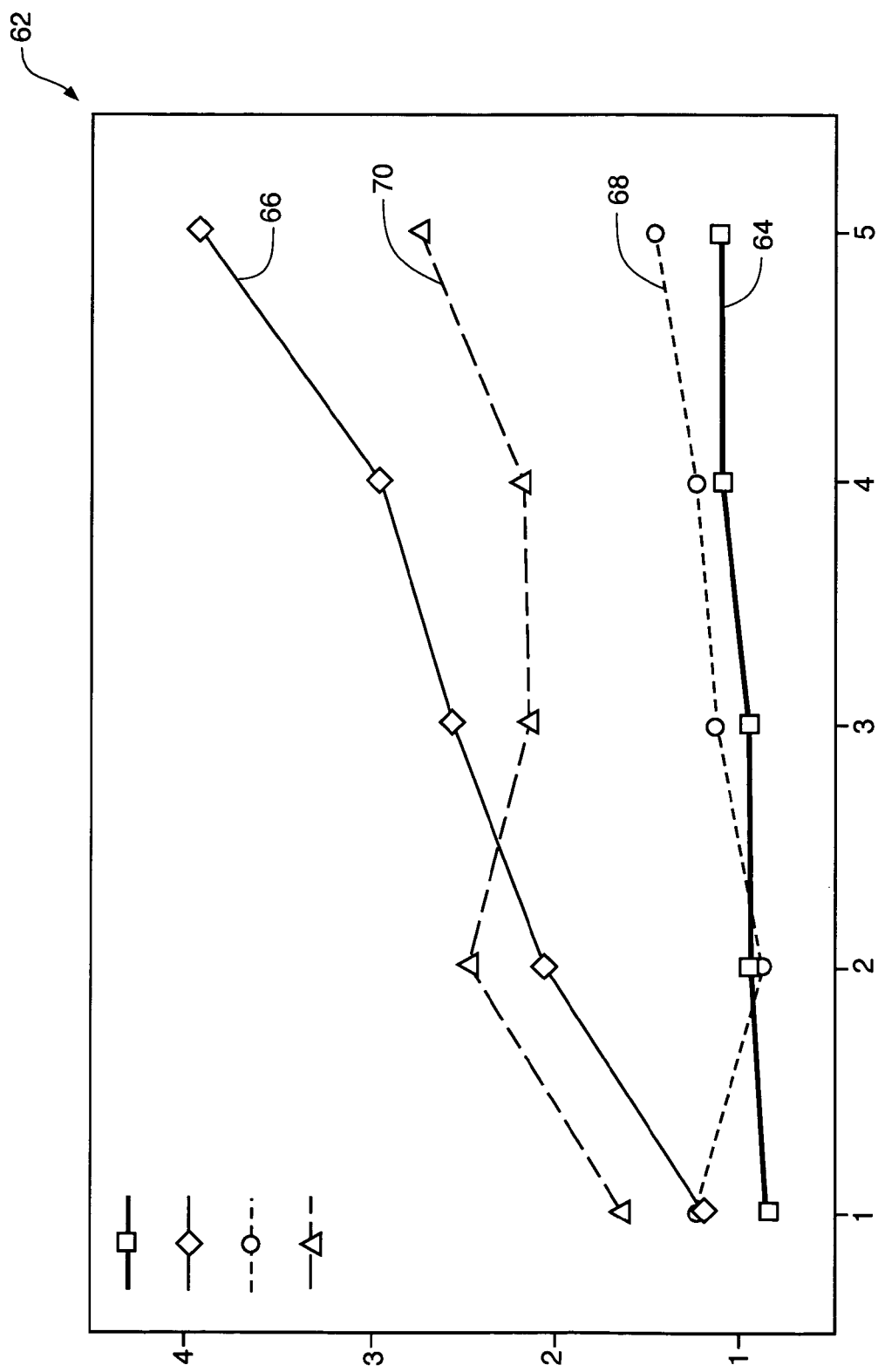
FIG. 5 is a graph of experimental results showing increased sodium excretion over time.

FIG. 5 depicts graph 62 showing experimental results for increased sodium excretion according to method 52 of the present disclosure achieved in animal subjects. Compared in graph 62 are four sets of data: control group 64, experimental group one 66, experimental group two 68, and experimental group three 70. For all four sets of data, renal excretion of sodium (_mol/kg/min–y axis) was measured as a function of time (x-axis) (where each collection period represents an additional fifteen minutes, collection period 1 is a baseline, and electrical stimulation was applied to experimental groups during collection period 2).

Control group 64 experienced no electrical stimulation, and as a consequence, demonstrated no substantial change in renal excretion over time. In contrast, experimental group one 66 experienced above-recited method 52 where stimulus strength equaled about 0.67 or 67% of motor threshold. For experimental group one 66, as well as all experimental groups, therapeutic electrical stimulation was applied during collection period 2 (15 minutes after baseline recording), but the effect on sodium excretion lasted a substantially longer time as shown at collection periods 3, 4 and 5, 15, 30, and 45 minutes, respectively after cessation of electrical stimulation. Experimental group two 68 also experienced above-recited method 52, but stimulus strength equaled about 0.90 or 90% of motor threshold. Experimental group two 68 demonstrated an insubstantial increase in renal excretion over time as compared to control group 64. Lastly, experimental group three 70 experienced above-recited method 52 where stimulus strength equaled about 0.6 volts (or about 34% of the mean motor threshold of 1.8 volts). Like experimental group one 66, experimental group three 70 experienced a dramatic and lasting increase in renal excretion of sodium and water. As evidenced by graph 62, electrical stimulation of dorsal spinal column 16 in accordance with method 52 results in a significant and lasting increase in renal excretion of sodium. Although the waveform, frequency, polarity, voltage and currents disclosed have been effective in animal experimentation some variation is tolerable without departing from the spirit of the disclosure. An optimal stimulation regime, including on times and off times for therapeutic electrical stimulation, will require further experimentation.

At the present time, it is postulated that electrical stimulation of the dorsal spinal column causes one or more changes in neuronal activity. First, it is possible that stimulation of the dorsal spinal column interrupts normal transmission of incoming pain information to the CNS by disrupting the electrical properties of afferent neurons carrying such pain information. Second, it is possible that stimulation of the dorsal spinal column forces normally afferent neurons to reverse their normal flow of information (retrograde transmission) and send outgoing signals to the kidney causing an increase in renal excretion. Third, it is possible that electrical stimulation of afferent neurons causes an increase or redistribution of blood flow in the kidney, thereby permitting the nephrons to decrease the reabsorption of sodium and thus increase the rate of excretion. Whatever the underlying physiology, the speed at which increased renal secretion is noted in experimental models (within 15 minutes after the onset of stimulation as shown in FIG. 5) suggests that renal hormones and the SNS are not involved.

The above theories are provided in an effort to explain the experimental results, but may be wrong or incomplete. Although the present invention has been described with reference to preferred embodiments, workers skilled in the art will recognize that changes may be made in form and detail without departing from the spirit and scope of the invention.

The invention claimed is:

1. A device comprising:
   a first electrode configured to be positioned on a dorsal spinal column at a vertebral level associated with sensory nerves of a kidney;
   a second electrode configured to be positioned in a paravertebral muscle proximate the first electrode; and
   a pulse generator in electrical communication with the first electrode and the second electrode for delivering an electrical current there between, the pulse generator programmed to determine a the motor threshold of the paravertebral muscle, and deliver a therapeutic electrical current between the first electrode and the second electrode, the therapeutic electrical current having an amplitude, duration, and waveform derived from, and expressed as a fraction of, the motor threshold of the paravertebral muscle, the therapeutic electrical current stimulating at least one afferent sensory neuron and causing a rapid increase in renal excretion of sodium.

2. The device of claim 1, wherein the amplitude is between about 30-90 percent of a motor threshold associated with the paravertebral muscle tissue.

3. The device of claim 2, wherein the amplitude is between about 50-80 percent of a motor threshold associated with the paravertebral muscle tissue.

4. The device of claim 1, wherein the electrical pulse has a frequency sufficient to cause the rapid increase in renal excretion of sodium as measured less than thirty minutes after initial delivery of the electrical pulse.

5. The device of claim 1, wherein the electrical pulse has a duration sufficient to cause the rapid increase in renal excretion of sodium as measured less than thirty minutes after initial delivery of the electrical pulse.

6. The device of claim 1, wherein the rapid increase in renal excretion of sodium is measurable less than 15 minutes after the stimulation.

7. The device of claim 1, wherein the rapid increase in renal excretion of sodium continues for a time after the stimulation concludes.

8. The device of claim 1, wherein the first electrode configured to be is positioned centrally on a dura matter surrounding the dorsal spinal cord such that the first electrode is capable of stimulating the at least one afferent neuron without stimulating efferent neurons.

9. A method comprising:
   placing a first electrode on a dorsal spinal column within a central nervous system at a vertebral level associated with sensory nerves from a kidney;
   placing a second electrode in a paravertebral muscle proximate the first electrode;

measuring a motor threshold of the paravertebral muscle with the second electrode to establish a motor threshold value; and applying an electrical current to at least one afferent sensory neuron with the first electrode, the electrical current having parameters derived from the motor threshold and less than the motor threshold value, wherein application of the electrical current causes a rapid increase in renal excretion of sodium as compared to a baseline taken before application of the electrical current.

10. The method of claim 9, further comprising:

terminating the application of electrical current to the first electrode, wherein the increased renal excretion of sodium continues for a time after the electrical current is terminated.

11. The method of claim 9, wherein the increased rate of renal excretion is measurable less than 30 minutes after the application of electrical current.

12. The method of claim 11, wherein the increased rate of renal excretion is measurable less than 15 minutes after the application of electrical current.

13. The method of claim 9, wherein the electrical current has an amplitude sufficient to activate the paravertebral muscle tissue surrounding the at least one electrode.

14. The method of claim 13, wherein the amplitude is approximately 30-90 percent of the motor threshold associated with contraction of the paravertebral muscle tissue.

15. The method of claim 14, wherein the electrical current has a frequency sufficient to cause the increase in renal excretion, wherein the increase in renal excretion is measurable less than 30 minutes after the application of electrical current.

16. The method of claim 15, wherein the electrical current has a duration sufficient to cause the increase in renal excretion, wherein the increase in renal excretion is measurable less than 30 minutes after the application of electrical current.

17. A method for increasing renal excretion, the method comprising:

placing an electrode on a dorsal spinal cord within a central nervous system;

applying an electrical current to the electrode, wherein the electrode is positioned and the electrical current is configured to stimulate an afferent neuron without stimulating an efferent neuron thereby causing an increase in renal excretion of sodium while having an insubstantial affect on a sympathetic nervous system.

18. The method of claim 17, further comprising:

measuring the renal excretion of sodium before and after application of the electrical current to verify the increase in renal excretion of sodium and water.

19. The method of claim 18, wherein the increase in renal excretion is measurable less than 30 minutes after the application of electrical current.

20. The method of claim 18, further comprising:

measuring renal hormones before and after application of the electrical current to verify the insubstantial affect on the sympathetic nervous system.

* * * * *